United States Patent [19]

Knoll et al.

[11] 4,035,491

[45] * July 12, 1977

[54] PHARMACEUTICAL COMPOSITION HAVING SYNERGISTIC ANALGESIC ACTIVITY AND CONTAINING AZIDOMORPHINE OR AZIDOCODEINE

[75] Inventors: Jozsef Knoll; Zsuzsanna Fürst; Zoltan Meszaros; Gábor Nagy; Agoston Dävid, all of Budapest; Rezsö Bognar, Debrecen; Sändor Makleit, Debrecen; Gyula Välovics, Tiszavasvari, all of Hungary

[73] Assignee: Chinoin Pharmaceutical and Chemical Works Ltd., Budapest, Hungary

[ * ] Notice: The portion of the term of this patent subsequent to July 13, 1993, has been disclaimed.

[21] Appl. No.: 700,782

[22] Filed: June 29, 1976

Related U.S. Application Data

[63] Continuation-in-part of Ser. No. 536,402, Dec. 26, 1974, Pat. No. 3,969,519.

[30] Foreign Application Priority Data

Dec. 29, 1973 Hungary .......................... 2251 1432

[51] Int. Cl.² ............ A61K 31/655; A61K 31/505; A61K 31/485

[52] U.S. Cl. ................. 424/226; 424/251; 424/260

[58] Field of Search ............................ 424/251, 226

[56] References Cited

U.S. PATENT DOCUMENTS 3,969,519   7/1976   Knoll et al. .................... 424/251

Primary Examiner—Sam Rosen
Attorney, Agent, or Firm—Karl F. Ross; Herbert Dubno

[57] ABSTRACT

A pharmaceutical composition with synergistic analgesic effect which comprises an effective amount of 6-desoxy-6-azido-14-hydroxy-7,8-dihydro morphine or codeine or an analgesically effective salt thereof and an effective amount of a compound

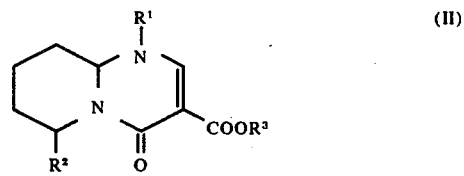

wherein $R^1$ and $R^2$ are lower alkyl and $R^3$ is hydrogen or lower alkyl, and the dotted lines represent hydrogenated or unsaturated bonds or an analgesically effective salt or quaternary compound thereof.

7 Claims, No Drawings

PHARMACEUTICAL COMPOSITION HAVING SYNERGISTIC ANALGESIC ACTIVITY AND CONTAINING AZIDOMORPHINE OR AZIDOCODEINE

This application is a continuation-in-part of Ser. No. 536,402 filed Dec. 26, 1974 (now U.S. Pat. No. 3,969,519).

The present invention relates to pharmaceutical compositions having synergistic analgesic activity and a process for the preparation thereof. For the relief of postoperational pain and in the case of cancer patients in an advanced stage of the disease, morphine and its derivatives are the most frequently used efficient analgesics. It is a wellknown fact, however, that in patients treated with morphine, the harmful side-effects, e.g. respiratory depression, tolerance and dependence develop in a relatively short time. The patient gets used to morphine and rapidly rising doses are required to obtain an equianalgesic effect; tolerance or dependence develops and the patient is in permanent need of the euphorizing effect of morphine. Another disadvantage of morphine is the fact that it is practically ineffective on oral application.

All the analgesics suited for the treatment of unbearable pain (e.g. cancer, postoperative, infarction, lithiases, etc.) are likely to induce the development of tolerance on chronic administration and their withdrawal produces severe — often fatal — somatic and psychic symptoms (physical and psychic dependence). It is generally accepted (Martin, 1967, Pharmaceutical Review 19, 463) that the appearance of tolerance and dependence necessarily accompany the action of the morphine-type drugs on the analgesic receptors. An analgesic equipotent to morphine, but devoid of its narcotic side-effects, has long been needed in clinical practice. For the replacement of morphine, 6-desoxy-6-azido-14-hydroxy-dihydro-isomorphine, prepared by Bognar and Makleit seems to be suitable.

According to the present invention there are provided pharmaceutical compositions having synergistic analgesic effects comprising at least one compound of the formula I or a salt thereof

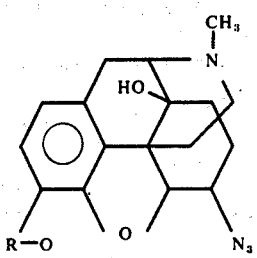

(wherein R is hydrogen or methyl) and at least one compound of the formula II

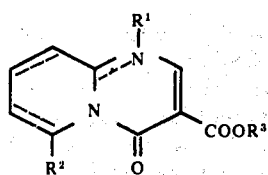

(wherein $R^1$ and $R^2$ are lower alkyl and $R^3$ is hydrogen or lower alkyl) in admixture with pharmaceutically acceptable inert solid or liquid carriers or diluents.

The present invention is based on the recognition that the compounds of the formula II

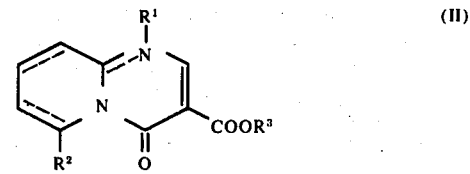

and their salts and quaternary salts potentiate the analgesic action of the azido compounds of the formula I

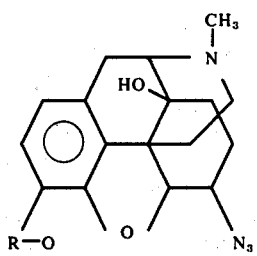

to a significant extent and also have an advantageous influence on their other properties. Thus, a well-expressed potentiation takes place and the effect of the combination surpasses the additive effect of the components when used alone.

A further advantage resides in the fact that the combinations according to the present invention are devoid of narcotic side effects.

In the compositions of the present invention a compound of the formula, I preferably 14-hydroxy-azido-7,8-dihydro-morphine may be used, but 14-hydroxy-azido-7,8-dihydro-codeine may be used with similar results too. The compound of the formula I may be used as the free base or in the form of an acid-addition salt thereof. The salts may be those formed with inorganic or organic acids; the acid component used must be pharmaceutically acceptable and should provide preferable solubility properties to the salt obtained. The bitartarate salts of the compounds of the formula I possess particularly advantageous solubility characteristics.

In the compounds of the formula II

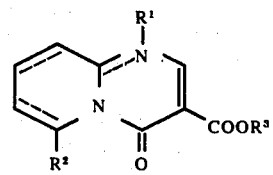

the alkyl groups may be straight or branched chain and contain 1 – 6, preferably 1 – 4 carbon atoms (e.g. methyl, ethyl, n-propyl, isobutyl, etc.). The salts and the quaternary salts of the compounds of the formula II may contain any pharmaceutically acceptable anion (e.g. inorganic anions, such as nitrate, chloride, bromide or sulphate anion; and organic anions, e.g. methylsulphate, ethylsulphate, etc.). A particularly preferred representative of the compounds of the formula II is the 1,6-dimethyl-3-carbethoxy-4oxo-6,7,8,9-tetrahydro-homopyrimidazolium-methosulphate.

Synergistic analgesic effect is measured by means of the analgesic tests (Knoll et al: Animal and Clinical Pharmaceutical Techniques in Drug Ev. [1967] 305 - 321).

This is a model test for surgical pains and demonstrates exclusively a major analgesic effect. The essence of the test is that under the effect of a 10 mg/kg i.v. dose of morphine, rats can be subjected to laparatomia without the slightest signs of pain, attempts to move and postoperational prostration. For each dose 10 rats each were used.

It has been found that the homopyrimidazole derivatives of the formula II and salts and quaternary salts thereof on the one hand, and the 14-hydroxy-azido-7,8-dihydro-morphine and 14-hydroxy-azido-7,8-dihydro-codeine on the other, potentiate the analgesic effect of each other to a significant extent without influencing the toxicity or other side effects. The present invention is based on the recognition that a mutual effect exists between the representatives of both compound groups.

The synergistic effect is shown on the examples of a composition containing 14-hydroxy-azido-7,8-dihydro-morphine (compound A) and 1,6-dimethyl-3-carbethoxy-4-oxo-6,7,8,9-tetrahydro-homopyrimidazolium-methosulphate (compound B) by using the algolytic test discussed above. The results are summarized in the following table;

Table I

| Compound A | Route of administration | Compound B | Route of administration | Algolytic test analgesic effect in % |
|---|---|---|---|---|
| 0.050 | i.v. | — | — | 15 |
| — | — | 75 | i.v. | 2 |
| 0.050 | i.v. | 75 | i.v. | 81 |
| 10 | p.o. | — | — | 18 |
| — | — | 250 | p.o. | 9 |
| 10 | p.o. | 250 | p.o. | 69 |

It appears from the data of the above table that both on intravenous and oral administration the combination containing doses of the components being ineffective per se (0.050 mg/kg) of compound A i.v. and 75 mg/kg i.v. of compound B, or 10 mg/kg p.o. of compound A and 250 mg/kg p.o. of compound B respectively produces a very strong analgesic effect being 81% in intravenous and 69% in oral administration.

The algolytic test is a measure exclusively of the analgesic effect of narcotics. For this reason, the said composition of the present invention is very valuable in the relief of surgical pains.

The synergistic effect of the pharmaceutical composition of the present invention is also proved by the hot-plate test, described by Woolfe and MacDonald (J. Pharm. 80, 300) and modified by Porszasz and Herr (Kiserl. Orvostud. 2, 292). This method is based on the measurement of radiating heat. The essence of the test is that rats without preliminary training are placed on plates having a temperature of 56° C and after a certain period, the time of appearance of certain pain reactions (blowing and licking of the paws) is measured. The analgesic effect is expressed in the percental prolongation of the reaction time of the control.

Table II

| Compound A | Route of administration | Compound B | Route of administration | Hot plate test analgesic effect in % |
|---|---|---|---|---|
| 0.025 | i.v. | — | — | 29 |
| — | — | 50 | i.v. | 14 |

Table II-continued

| Compound A | Route of administration | Compound B | Route of administration | Hot plate test analgesic effect in % |
|---|---|---|---|---|
| — | — | 75 | i.v. | 49 |
| 0.025 | i.v. | 50 | i.v. | 68 |
| 0.025 | i.v. | 75 | i.v. | 97 |
| 10.0 | p.os | — | — | 21 |
| — | — | 250 | p.os | 32 |
| 10.0 | p.os | 250 | -.os | 92 |

It may be seen from the above table that the homopyrimidazole-derivative increases the analgesic effect of compound A to a significant extent. This is well proved by the experiment in which the two compounds are added simultaneously intravenously (0.025 mg/kg and 50 mg/kg respectively) or orally (10 mg/kg and 250 mg/kg respectively). From the point of view of practical therapy the latter may be of great importance, since it is well-known the derivatives of morphine when administered orally, show low activity and the strong peroral assuaging of pain is an undissolved problem. The effective intravenous combinations may be used in operation narcosis and the introduction thereof.

The mutual effect between azidomorphine derivatives and homopyrimidazole derivatives has been demonstrated in several pharmacological tests. In pain relief, a potentiating synergism has been proved. Further, it will be shown that the synergism of the analgesic effect is not accompanied by a synergism of undesired side-effects (e.g. central nerval depressive effect).

The central nerval depressive effect is tested on the modified spring test (J. Knoll: Publications of the Hungarian Academy of Sciences 14,223). In earlier publications (Knoll, 1967; Screening and grouping of psycho-pharmacologic agents in: Animal and Clinical Pharm. Techn. in Drug Ev. 2, Ed.s.: Siegler, P. E. and Moyer, J. H. Year Book Medical Publ. Chicago, 1967, pp. 305–321.: Knoll et al: 1967, Arzneimittelforschung 21, (1971) 717–738) we have pointed out that while in the modified spring test morphine derivatives inhibit the defence reaction and escape of the animals when administered even in therapeutical doses exerting an analgesic effect, the homopyrimidazoles exhibit said effect but in sub-toxical doses. The synergistic combinations were tested under subcutaneous and oral administration. The mutuality and many-sidedness of the synergism was determined too.

The results are summarized in the following table:

Table III

| Compound A mg/kg | Route of administration | Compound A mg/kg | Route of administration | Activity | |
|---|---|---|---|---|---|
| | | | | % | index |
| 0.025 | s.c. | — | — | 0 | 8 |
| — | — | 50 | s.c. | 0 | 7.6 |
| 0.025 | s.c. | 50 | s.c. | 20 | 6.2 |
| 5 | p.os | — | — | 0 | 8.8 |
| — | — | 150 | p.os | 0 | 8.8 |
| 5 | p.os | 150 | p.os | 40 | 5.0 |

Thus, in the modified spring test the combination of 14-hydroxy-azido-7,8-dihydromorphine and 1,6-dimethyl-4-oxo-3-ethoxycarbonyl-6,7,8,9-tetrahydro-homopyrimidazolium-methosulphate results a simple addition of the effect of the components in the place of the synergistic potentiating observed in the analgesic effect.

Similarly to 14-hydroxy-azido-7,8-dihydromorphine, a synergism has been demonstrated with the combination of 14-hydroxy-azido-7,8-dihydrocodeine (compound C) and 1,6-dimethyl-3-carbethoxy-4-oxo-6,7,8,9-tetrahydro-homopyrimidazolium-methosulphate as well.

The results are summarized in the following table:

Table IV

| Compound C mg/kg | Route of administration | Compound B mg/kg | Route of administration | Hot plate test % | Modified spring test % | index |
|---|---|---|---|---|---|---|
| 0.25 | s.c. | — | — | — | 20 | 6.2 |
| 0.5 | s.c. | — | — | 17 | — | — |
| 1.0 | s.c. | — | — | 35 | — | — |
| — | — | 50 | s.c. | 13 | — | — |
| — | — | 75 | s.c. | 49 | 20 | 5.6 |
| 0.5 | s.c. | 50 | s.c. | 86 | — | — |
| 0.125 | s.c. | 75 | s.c. | — | 20 | 6.2 |
| 0.125 | s.c. | 100 | s.c. | — | 40 | 4.6 |
| 2.5 | p.os | — | — | — | 0 | 8.2 |
| 3.75 | p.os | — | — | — | 0 | 6.8 |
| 5.0 | p.os | — | — | — | 40 | 5.2 |
| 2.5 | p.os | 50 | p.os | — | 0 | 8.2 |
| 2.5 | p.os | 100 | p.os | — | 50 | 4.4 |

The values of the above table show a synergism of analgesic effect similar to 14-hydroxy-azido-7,8-dihydromorphine (14-hydroxy-azido-7,8-dihydrocodeine, 0.5 mg/kg s.c. and 50 mg/kg of compound B s.c.), while the central depressive effect of the combination does not exceed the additive effect of the components.

In the following test compound B has been replaced by the following representative derivatives of the homopyrimidazole compounds of the formula II.

Compound A = 14-hydroxy-azido-7,8-dihydro-morphine

Compound B = 1,6-dimethyl-3-ethoxycarbonyl-4-oxo-6,7,8,9-tetrahydro-homopyrimidazolium-methosulphate Compound C = 14-hydroxy-azido-7,8-dihydrocodeine Compound D = 1,6-dimethyl-3-ethoxycarbonyl-4-oxo-1,6,7,8,9,10-hexahydro-homopyrimidazole Compound E = 6-methyl-3-ethoxycarbonyl-4-oxo-6,7,8,9-tetrahydro-homopyrimidazole Compound F = 1,6-dimethyl-3-ethoxycarbonyl-4-oxo-6,7,8,9-tetrahydro-homopyrimidazole.

The results obtained are summarized in the following table.

Table V

| Compound A mg/kg | Compound B mg/kg | Homopyrimidazole Compound | Dose | Hot plate test % |
|---|---|---|---|---|
| 0.025 i.v. | — | — | — | 29 |
| — | — | E | 200 i.v. | 20 |
| — | — | — | 300 i.v. | 72 |
| 0.025 i.v. | — | E | 200 i.v. | 39 |
| — | — | F | 300 i.v. | 24 |
| — | — | — | 400 i.v. | 61 |
| 0.025 i.v. | — | F | 300 i.v. | 48 |
| — | — | D | 50 i.v. | 39 |
| 0.025 i.v. | — | D | 50 i.v. | 52 |
| — | 0.5 s.c. | — | — | 17 |
| — | — | E | 200 s.c. | 27 |
| — | 0.5 s.c. | E | 200 s.c. | 26 |
| — | — | D | 50 s.c. | 22 |
| — | 0.5 s.c. | D | 50 s.c. | 55 |
| — | — | F | 300 s.c. | 28 |
| — | 0.5 s.c. | F | 300 s.c. | 27 |

The above data show that synergism is also present in combinations comprising a compound of the formula I and a compound of the formula II, other than compound B, but the best results were achieved when using compositions comtaining a compound of the formula I and 1,6-dimethyl-3-carbethoxy-4-oxo-6,7,8,9-tetrahydro-homopyrimidazolium-methosulphate.

A further advantage of the composition of the present invention is that the central depression effect of the composition does not surpass the additive effect of the components.

The homopyrimidazole derivatives of the formula II and salts and quaternary salts thereof and also the preparation of these compounds is described in our British Pat. No. 1 209 946.

The relative amount of the active ingredients in the combination according to the present invention may vary within a wide range. It may be stated that the composition may contain about 20 – 1000, preferably 100 – 1000, particularly 300 – 1000 parts by weight of a compound of the formula II related to 1 part by weight of an azido-compound of the formula I. In oral, parenteral compositions of the said ratio may be about 100:0 – 1000:1, while in oral compositions about 20:1 – 100:1.

The pharmaceutical compositions of the formula I may be finished in dosage forms suitable for oral or parenteral administration. The oral forms may be tablets, capsules, pills, coated pills, etc., while the parenteral dosage forms may be injectable preparations, powder ampouls, etc.

The pharmaceutical compositions of the present invention comprising 14-hydroxy-azido-7,8,-dihydrocodeine or a salt thereof as compound of the formula I are suitable for oral administration (tablets, capsules) too. This oral dosage form is particularly advantageous, since in the clinical practice of analgesics of the morphine type it enables the elimination of the injection treatment, which is very uncomfortable and painful, for the first time. The said oral composition comprises preferably about 20 – 100 parts by weight, particularly preferably 30 parts by weight of a compound formula II calculated on 1 part by weight of azido-compound or the bitartarate thereof. A highly preferred embodiment of the present invention is a tablet or capsule comprising about 100 – 250 mg. particularly 150 mg., of 1,6-dimethyl-3-carbethoxy-4-oxo-6,7,8,9-tetrahydro-homopyrimidazolium-methosulphate and 2.5 – 10 mg., preferably 5 mg. of 14-hydroxy-azido-7,8-dihydrocodeine on the bitartarate thereof.

The parenteral compositions according to the present invention contain preferably 100 – 1000 parts by weight of a compound of the formula II related to 1 part by weight of an azido-compound of the formula I. A very preferred embodiment of the present invention is a parenteral composition (injectable solution, powder ampouls) comprising about 75 – 500 mg. of 1,6-dimethyl-3-carbethoxy-4-oxo-6,7,8,9-tetrahydro-homopyrimidazolium-methosulphate and about 0.2 – 0.5 mg. of azido-derivative.

The synergistic compositions of the present invention may be prepared by methods of the pharmaceutical industry known per se. The composition by admixing the active ingredient with inert non-toxic carriers or diluents (e.g. cellulose, silicic acid, stearine, polyvinylpyrrolidone, talc, starch, etc.). The said compositions may also contain wellknown additives (e.g. emulsifying, suspending agents, dyes, salts for controlling the osmotic pressure, buffers, etc.).

The parenteral compositions of the present invention may be prepared in aqueous or non-aqueous medium. The non-aqueous preparations may be prepared in propylene glycol, polyethylene glycol or any other suitable solvents. Powder ampouls may be prepared preferably by introducing a homopyrimidazole derivative of the formula II into a powder ampoule, dissolving an azido-compound of the formula I in distilled water or in a suitable non-aqueous medium, in a solvent ampoule and dissolving a homopyrimidazole derivative of the powder ampoule before use in the content of the solvent ampoule.

The preferred dosage in human therapy amounts to 1 capsule or 1 injection described above. The total daily dosage may consist of three or four single doses as defined above. These data are, however, mainly of informative character, and the dosage may be lower or higher, than the said data depending on the circumstances of the given case, the condition of the patient and the prescription of the physician.

EXAMPLE I 500 mg of 1,6-dimethyl-3-carbethoxy-4-oxo-6,7,8,9-tetrahydro-homopyrimidazolium-methosulphate are filled into a powder ampoule. 0.5 mg of 14-hydroxy-azido-7,8-dihydromorphine are dissolved in 5 ml of distilled water. Before use, the homopyrimidazole derivative being present in the powder ampoule is dissolved in the contents of the solvent ampoule. The composition is suitable for intravenous administration. In use at surgical intervention the proposed dose is one ampoule.

EXAMPLE II

| | |
|---|---|
| 1,6-dimethyl-3-carbethoxy-4-oxo-6,7,8,9-tetrahydro-homopyrimidazolium-methosulphate | 75 mg |
| 14-hydroxy-azido-7,8-dihydromorphine-bitartarate | 0.5 mg |
| Distilled water ad q.s. | 2 ml. |

The injectable solution thus obtained is filled into ampoules.

EXAMPLE III

A parenteral preparation having the following composition is prepared:

| | |
|---|---|
| 1,6-dimethyl-3-carbethoxy-4-oxo-6,7,8,9-tetrahydro-tetrahydro-homopyrimidazolium-methosulphate | 150 mg |
| 14-hydroxy-azido-7,8-dihydromorphine-bitartarate | 0.5 mg |
| Propylene glycol | 0.66 ml |
| Polyethylene glycol | 0.66 ml |
| Cellosolve | 0.66 ml |

The injectable solution thus obtained is filled into ampoules. The solution thus obtained is very stable; during storage at 20° C for 5 years, the decomposition is but a few percent.

EXAMPLE IV

According to known methods of pharmaceutical industry, capsules having the following composition are prepared:

| | |
|---|---|
| 14-hydroxy-azido-7,8-dihydrocodeine | 5 mg |
| 1,6-dimethyl-3-carbethoxy-4-oxo-6,7,8,9-tetrahydro-homopyrimidazolium-methosulphate | 150 mg |
| Colorant (dye) | 1 mg |
| Titanium dioxide | 3 mg |
| Betaine hydrochloride | 3 mg |
| Colloidal silicic acid | 13 mg |
| Polyvinylpyrrolidone | 15 mg |
| Stearine | 26 mg |
| Crystalline cellulose | 76 mg. |

EXAMPLE V

Test Method:
Hot plate test, Woolfe and McDonald, A. P., J. Pharm. 80 (1944) 300; modified by Porszasz and Mr. F. Kiserl.-Orvostud. 2 (1950) 292.

Test animal:
rat.

The following test compounds are used:
Probone = 1,6-dimethyl-3-ethoxycarbonyl-4-oxo-6,7,8,9-tetrahydro-homopyrimidazolium-methosulphate (compound of the Formula II),
Algopyrin = 2,3-dimethyl-4-methylamino-1-phenyl-5-pyrazolone-N-methanesulphonic acid,
Aspirin = 0-acetyl salicylic acid,
Amidazophen = 4-dimethylamino-2,3-dimethyl-1-phenyl-3-pyrazoline-5-one.

| 14-hydroxy-7,8-dihydro-azidomorphine μg/kg | Administration | Minor Analgeticum Name | mg/kg | Administration | Analgesic effect % |
|---|---|---|---|---|---|
| 12.5 | s.c. | — | — | — | 17 |
| 25.0 | s.c. | — | — | — | 28 |
| — | — | Algopyrin | 150 | s.c. | 27 |
| — | — | Algopyrin | 200 | s.c. | 41 |
| — | — | Aspirin | 200 | p.os | 17 |
| — | — | Aspirin | 300 | p.os | 45 |
| 12.5 | s.c. | Algopyrin | 150 | s.c. | 31 |
| 25.0 | s.c. | Algopyrin | 150 | s.c. | 41 |
| 12.5 | s.c. | Aspirin | 200 | p.os | 22 |
| 25.0 | s.c. | Aspirin | 200 | p.os | 48 |

It may be seen from the above Table that compound Algopyrin and Aspirin, the two most widely used minor analgesics, when applied in a dose inactive per se do not potentiate the analgesic effect of 14-hydroxy-7,8-dihydroazidomorphine. The effect of the said combinations does not even reach the addition of the effect of the components used per se. This means that known potentiators cannot be improved upon as analgesics in combination with 14-hydroxy-7,8-dihydroazidomorphines of the Formula I.

The following test report shows that while the narcosis potentiating effect of 14-hydroxy-7,8-dihydroazidomorphine is increased to a significant extent by the compounds of the Formula II, this effect cannot be achieved by usual minor analgesics.

| 14-hydroxy-azido-7,8-dihydromorphene-dose μ/kg | Minor analgesic Name | mg/kg | Prolongation of narcosis time % |
|---|---|---|---|
| 12.5 i.v. | — | — | 408 |
| 25.5 i.v. | — | — | 510 |
| — | Probon | 50 i.v. | 287 |
| 12.5 i.v. | Probon | 50 i.v. | 760 |
| | Amidazophen | 150 s.c. | 85 |
| | Aspirin | 200 p.os | 65 |
| 12.5 i.v. | Amidazophen | 150 s.c. | 89 |
| 12.5 i.v. | Aspirin | 200 p.os | 75. |

These tests demonstrate that, for reasons which are not fully understood, 14-hydroxy-7,8-dihydroderivatives of azido-morphine and azidocodeine are not potentiated synergistically by compounds of the Formula II of the application.

We claim:

1. A pharmaceutical composition of synergistic analgesic effect which comprises an effective amount of 6-desoxy-6-azido-14-hydroxy-7,8-dihydro-morphine or codeine or an analgesically effective salt thereof and an effective amount of a compound of the formula

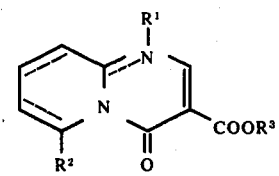

wherein $R^1$ and $R^2$ are lower alkyl and $R^3$ is hydrogen or lower alkyl, and the dotted lines represent hydrogenated or unsaturated bonds or an analgesically effective salt or quaternary compound thereof.

2. The pharmaceutical composition defined in claim 1 wherein the morphine or codeine is in the form of its bitartarate.

3. The pharmaceutical composition defined in claim 1 wherein the compound of said formula is 1,6-dimethyl-3-carbethoxy-4-oxo-6,7,8,9-tetrahydro-homopyrimidazolium-methosulphate.

4. The pharmaceutical composition defined in claim 1, which comprises 100 to 1000 parts by weight of said formula or its salt or quaternary compound per part by weight of the morphine or codeine.

5. The pharmaceutical composition defined in claim 1, which comprises 20 to 100 parts by weight of 1,6-dimethyl-3-carbethoxy-4-oxo-6,7,8,9-tetrahydro-homopyrimidazolium-methosulphate per part by weight of 14-hydroxy-azido-7,8-dihydro-codeine or a salt thereof.

6. The pharmaceutical composition defined in claim 1, which comprises 20 to 100 parts by weight of 1,6-dimethyl-3-carbethoxy-4-oxo-6,7,8,9-tetrahydro-homopyrimidazolium-methosulphate per part by weight of 14-hydroxy-azido-7,8-dihydro-morphine or a salt thereof.

7. A method for relieving of pain in humans, which comprises administering to the patient a pharmaceutical composition as defined in claim 1.

* * * * *